United States Patent
Lesch et al.

(10) Patent No.: US 12,420,066 B2
(45) Date of Patent: *Sep. 23, 2025

(54) IMAGE GUIDED SURGERY SYSTEM GUIDE WIRE AND METHODS OF MANUFACTURING AND USE

(71) Applicant: Entellus Medical, Inc., Plymouth, MN (US)

(72) Inventors: Paul Lesch, Lino Lakes, MN (US); Alexander Houck, Hopkins, MN (US); Aaron Pidde, Bloomington, MN (US); Matt Higgins, Maple Grove, MN (US)

(73) Assignee: Stryker Corporation, Portage, MI (US)

(*) Notice: Subject to any disclaimer, the term of this patent is extended or adjusted under 35 U.S.C. 154(b) by 253 days.

This patent is subject to a terminal disclaimer.

(21) Appl. No.: 18/177,958

(22) Filed: Mar. 3, 2023

(65) Prior Publication Data

US 2023/0226325 A1 Jul. 20, 2023

Related U.S. Application Data

(63) Continuation of application No. 17/020,077, filed on Sep. 14, 2020, now Pat. No. 11,617,866.
(Continued)

(51) Int. Cl.
*A61M 25/09* (2006.01)
*A61M 29/02* (2006.01)

(52) U.S. Cl.
CPC ............ *A61M 25/09* (2013.01); *A61M 29/02* (2013.01); *A61M 2025/09141* (2013.01);
(Continued)

(58) Field of Classification Search
CPC ........... A61B 2017/00867; A61B 2017/22038; A61B 2017/00946; A61B 2034/2051;
(Continued)

(56) References Cited

U.S. PATENT DOCUMENTS 7,720,521 B2 5/2010 Chang et al.
8,109,953 B1 2/2012 King, III et al.
(Continued)

FOREIGN PATENT DOCUMENTS

CN 104244816 A 12/2014
CN 109996502 A 7/2019
(Continued)

OTHER PUBLICATIONS

Office Action issued by the Canadian Patent Office in Canadian Application No. 3,154,493 dated Jan. 4, 2024.
(Continued)

*Primary Examiner* — Deanna K Hall
(74) *Attorney, Agent, or Firm* — McDonnell Boehnen Hulbert & Berghoff LLP

(57) ABSTRACT

The present disclosure provides a guide wire system comprising (a) a guide wire having a distal end and a proximal end, wherein the guide wire comprises a superelastic material, (b) a first connector coupled to the proximal end of the guide wire, (c) a second connector coupled to the guide wire between the distal end and the proximal end, (d) an electromagnetic sensor coupled to the distal end of the guide wire, and (e) a polymeric tube surrounding the guide wire and at least a portion of the electromagnetic sensor.

10 Claims, 8 Drawing Sheets

Related U.S. Application Data

(60) Provisional application No. 62/899,999, filed on Sep. 13, 2019.

(52) U.S. Cl.
CPC .............. *A61M 2025/0915* (2013.01); *A61M 2025/09183* (2013.01); *A61M 2029/025* (2013.01); *A61M 2205/0222* (2013.01); *A61M 2205/3317* (2013.01); *A61M 2210/0681* (2013.01)

(58) Field of Classification Search
CPC ................ A61B 34/20; A61B 90/98; A61M 2025/09141; A61M 2025/0915; A61M 2029/025; A61M 2205/0222; A61M 25/09; A61M 2205/3317; A61M 2210/0681
See application file for complete search history.

(56) References Cited

U.S. PATENT DOCUMENTS

| | | | |
|---|---|---|---|
| 11,135,406 B2 | 10/2021 | Ribelin et al. | |
| 11,617,866 B2 * | 4/2023 | Lesch .................. | A61B 90/98 604/164.13 |
| 2002/0095137 A1 | 7/2002 | Zadno-Azizi et al. | |
| 2006/0004286 A1 | 1/2006 | Chang et al. | |
| 2006/0173382 A1 | 8/2006 | Schreiner | |
| 2006/0270948 A1 | 11/2006 | Viswanathan et al. | |
| 2007/0208252 A1 | 9/2007 | Makower | |
| 2008/0255446 A1 | 10/2008 | Akins | |
| 2009/0234328 A1 | 9/2009 | Cox et al. | |
| 2011/0152721 A1 | 6/2011 | Sela et al. | |
| 2011/0218520 A1 | 9/2011 | Andrich | |
| 2012/0172761 A1 | 7/2012 | Meller et al. | |
| 2013/0018359 A1 | 1/2013 | Coyle | |
| 2013/0296692 A1 | 11/2013 | Vanney et al. | |
| 2014/0100552 A1 | 4/2014 | Gallacher et al. | |
| 2014/0200444 A1 | 7/2014 | Kim et al. | |
| 2015/0119923 A1 | 4/2015 | Liberatore | |
| 2016/0082233 A1 | 3/2016 | Ha et al. | |
| 2017/0007281 A1 | 1/2017 | Goldfarb et al. | |
| 2017/0259048 A1 | 9/2017 | Matlock et al. | |
| 2019/0060614 A1 | 2/2019 | Hebert | |
| 2019/0175888 A1 | 6/2019 | Abdelwahed et al. | |
| 2019/0192177 A1 | 6/2019 | Palushi et al. | |
| 2019/0261886 A1 | 8/2019 | King et al. | |
| 2019/0262512 A1 | 8/2019 | Palushi et al. | |
| 2020/0254230 A1 | 8/2020 | Sheng et al. | |
| 2021/0077788 A1 | 3/2021 | Lesch et al. | |

FOREIGN PATENT DOCUMENTS

| | | |
|---|---|---|
| JP | H09-051954 A | 2/1997 |
| JP | 2008-264533 A | 11/2008 |
| JP | 2018-516623 A | 6/2018 |
| KR | 101831659 B1 | 2/2018 |
| WO | 2016/165943 A1 | 10/2016 |
| WO | 2017/156086 A1 | 9/2017 |
| WO | 2019/073571 A1 | 4/2019 |
| WO | 2019/075634 A1 | 4/2019 |
| WO | 2010/022370 A1 | 2/2020 |

OTHER PUBLICATIONS

Examination Report No. 1 issued by the Australian Patent Office in Application No. 2020346080 dated May 22, 2023 2020 (7 Pages).
Office Action issued by the Japanese Patent Office in application No. 2022-516351 dated Jul. 5, 2024, English translation included.
Notice of Grant issued by the Chinese Patent Office in application No. 202080062655.5 dated Dec. 13, 2024.
First Office Action issued by the Chinese Patent Office in Chinese Application No. 2020800626555 dated Aug. 9, 2024. (English translation included).
International Search Report and Written Opinion issued by the European Search Office in International Application No. PCT/US2020/050675 dated Nov. 18, 2020 (30 Pages).
Decision of Rejection issued by the Japanese Patent Office in application No. 2022-516351 dated Dec. 26, 2024.
Communication Pursuant to Article 94(3) EPC issued by the European Search Office in European Application No. 20 781 663.8 dated Sep. 6, 2023.
Reconsideration Report issued by the Japanese Patent Office in application No. 2022-516351 dated May 28, 2025.

* cited by examiner

IMAGE GUIDED SURGERY SYSTEM GUIDE WIRE AND METHODS OF MANUFACTURING AND USE

RELATED APPLICATIONS

This application is a Continuation of U.S. application Ser. No. 17/020,077, filed on Sep. 14, 2020, which claims priority to U.S. Provisional Application No. 62/899,999, filed on Sep. 13, 2019, the entire contents of all of which are hereby incorporated by reference.

FIELD

The present invention relates generally to a guide wire system and more particularly to guide wire systems and methods of manufacture and use that are useable in conjunction with image guided surgery systems to facilitate insertion and positioning of various other apparatus at desired locations within the body, in particular the sinus cavities.

BACKGROUND

Unless otherwise indicated herein, the materials described in this section are not prior art to the claims in this application and are not admitted to be prior art by inclusion in this section.

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent acute sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state via the use of a guide wire that is positioned in the desired nasal cavity using an image guided surgery system. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

While guide wire systems exist for use in placement of nasal treatment devices, improved guide wire systems, methods of manufacture, and methods of use may be desirable.

SUMMARY

The present disclosure is related to guide wire systems, methods of manufacture, and methods of use. More specifically, the present disclosure relates to guide wire systems for use in combination with image guided surgery systems for treating nasal afflictions such as sinusitis.

In one example, the present disclosure provides a guide wire system. The guide wire system includes a guide wire having a distal end and a proximal end, wherein the guide wire comprises a superelastic material that is configured to (i) transition from a first configuration to a second configuration responsive to a force applied to the guide wire and (ii) return from the second configuration to the first configuration responsive to the force being removed from the guide wire. The guide wire system also includes a first connector coupled to the proximal end of the guide wire. The guide wire system also includes a second connector coupled to the guide wire between the distal end and the proximal end. The guide wire system also includes an electromagnetic sensor coupled to the distal end of the guide wire. The guide wire system also includes a polymeric tube surrounding at least a portion of the guide wire and at least a portion of the electromagnetic sensor.

In another example, the present disclosure provides a method manufacturing a guide wire system. The method includes positioning a first connector at a proximal end of a guide wire, wherein the guide wire comprises a superelastic material that is configured to (i) transition from a first configuration to a second configuration responsive to a force applied to the guide wire and (ii) return from the second configuration to the first configuration responsive to the force being removed from the guide wire. The method also includes positioning a second connector on the guide wire between a distal end of the guide wire and the proximal end of the guide wire. The method also includes positioning an electromagnetic sensor at the distal end of the guide wire. The method also includes positioning a polymeric tube around at least a portion of the guide wire and at least a portion of the electromagnetic sensor. The method also includes applying a heat source to at least a portion of the polymeric tube.

In yet another example, the present disclosure provides a method of treating a sinus cavity of a subject. The method includes inserting a distal portion of a guide wire system into a lumen of a balloon dilation catheter, the guide wire system including: (i) a guide wire having a distal end and a proximal end, wherein the guide wire comprises a superelastic material that is configured to (1) transition from a first configuration to a second configuration responsive to a force applied to the guide wire and (2) return from the second configuration to the first configuration responsive to the force being removed from the guide wire, (ii) a first connector coupled to the proximal end of the guide wire, (iii) a second connector coupled to the guide wire between the distal end and the proximal end, (iv) an electromagnetic sensor coupled to the distal end of the guide wire, and (v) a polymeric tube surrounding at least a portion of the guide wire and at least a portion of the electromagnetic sensor, and the balloon dilation catheter including: (i) an inner guide member including the lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member. The method also includes coupling the second connector of the guide wire system to the balloon dilation catheter such the distal end of the guide wire is fixed with respect to a distal end of the balloon dilation catheter. The method also includes directing the distal end of the guide wire and the distal end of the balloon dilation catheter simultaneously to a drainage pathway of the sinus cavity using data received from the electromagnetic sensor. The method also includes inflating the balloon.

These as well as other aspects, advantages, and alternatives, will become apparent to those of ordinary skill in the art by reading the following detailed description, with reference where appropriate to the accompanying drawings.

DETAILED DESCRIPTION

Figure 1:
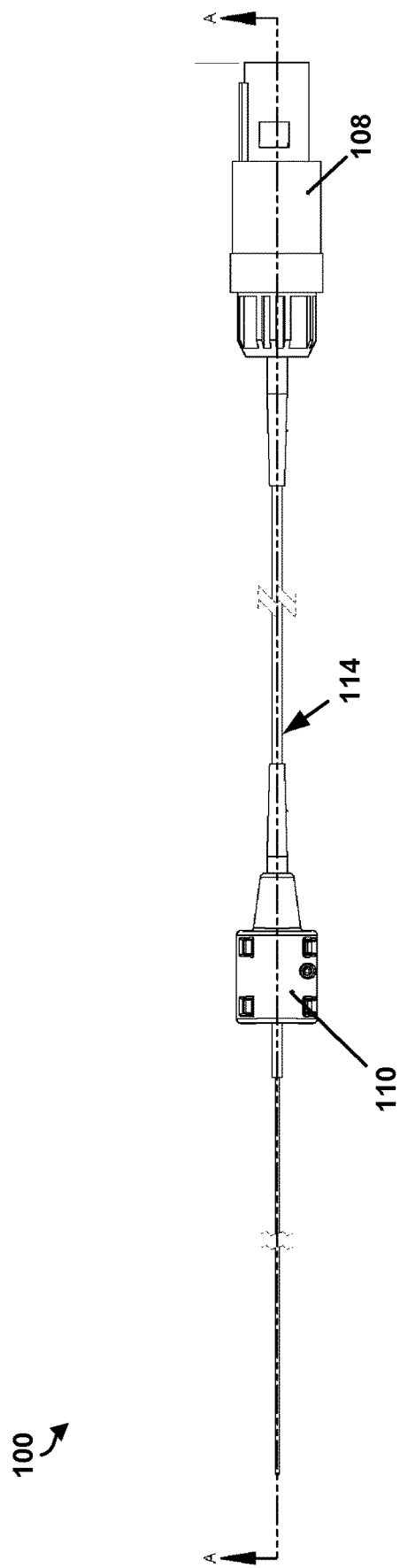
FIG. 1 is side view of the guide wire, according to an example.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112(f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Illustrative, non-exhaustive examples, which may or may not be claimed, of the subject matter according the present disclosure are provided below.

Figure 2:
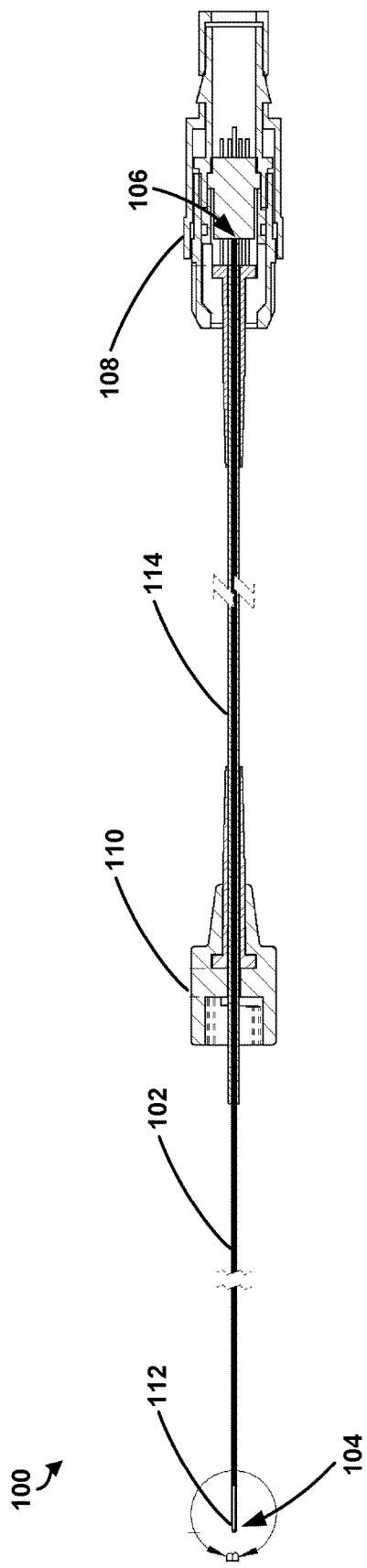
FIG. 2 is a cross-sectional view taken along line A-A of the guide wire system of FIG. 1, according to an example.
Figure 3:
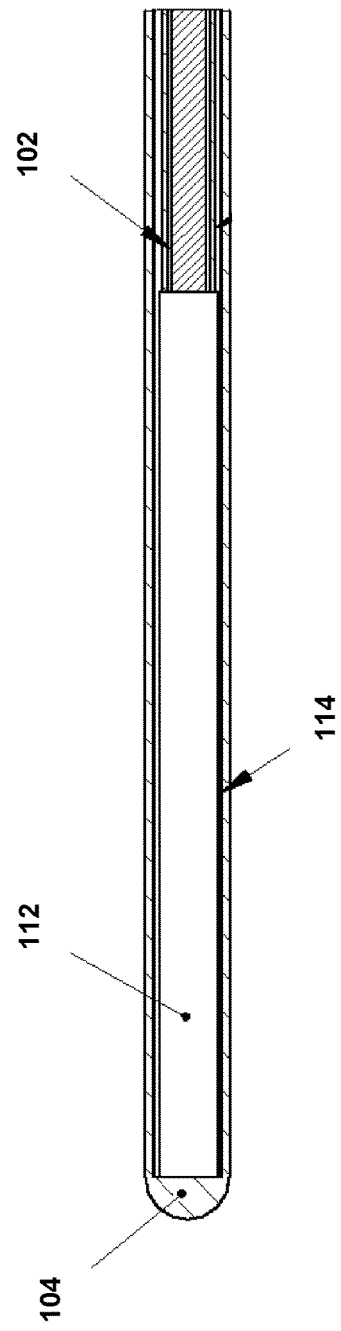
FIG. 3 is a detailed cross-sectional view of the distal end of the guide wire system of FIG. 2, according to an example.
Figure 4:
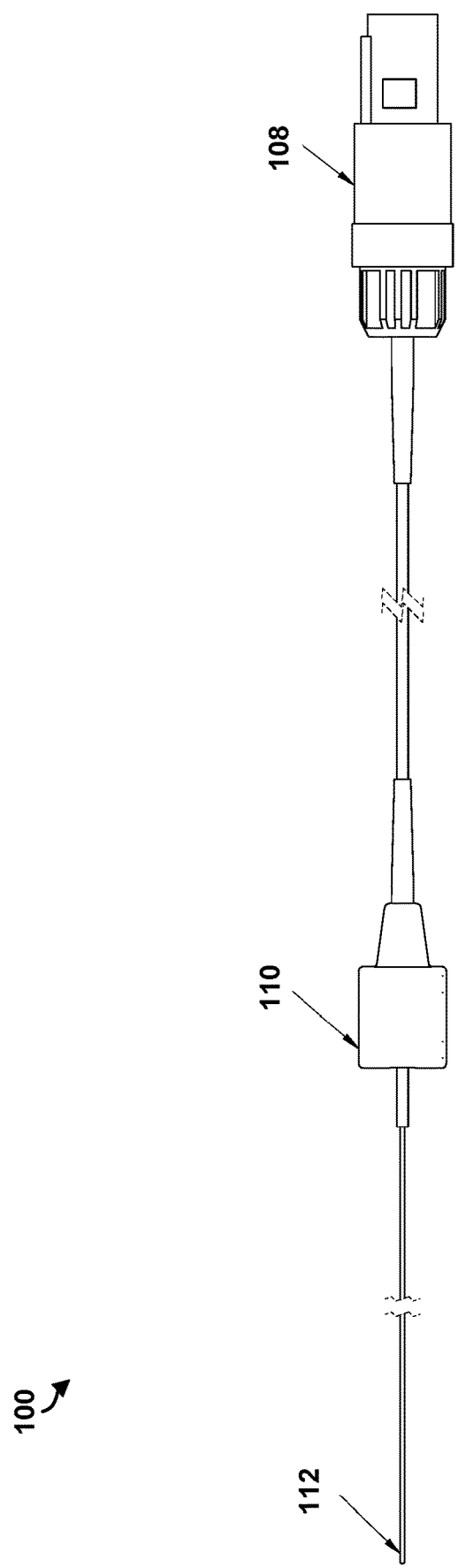
FIG. 4 is a perspective view of the guide wire system of FIG. 1, according to an example.
Figure 5:
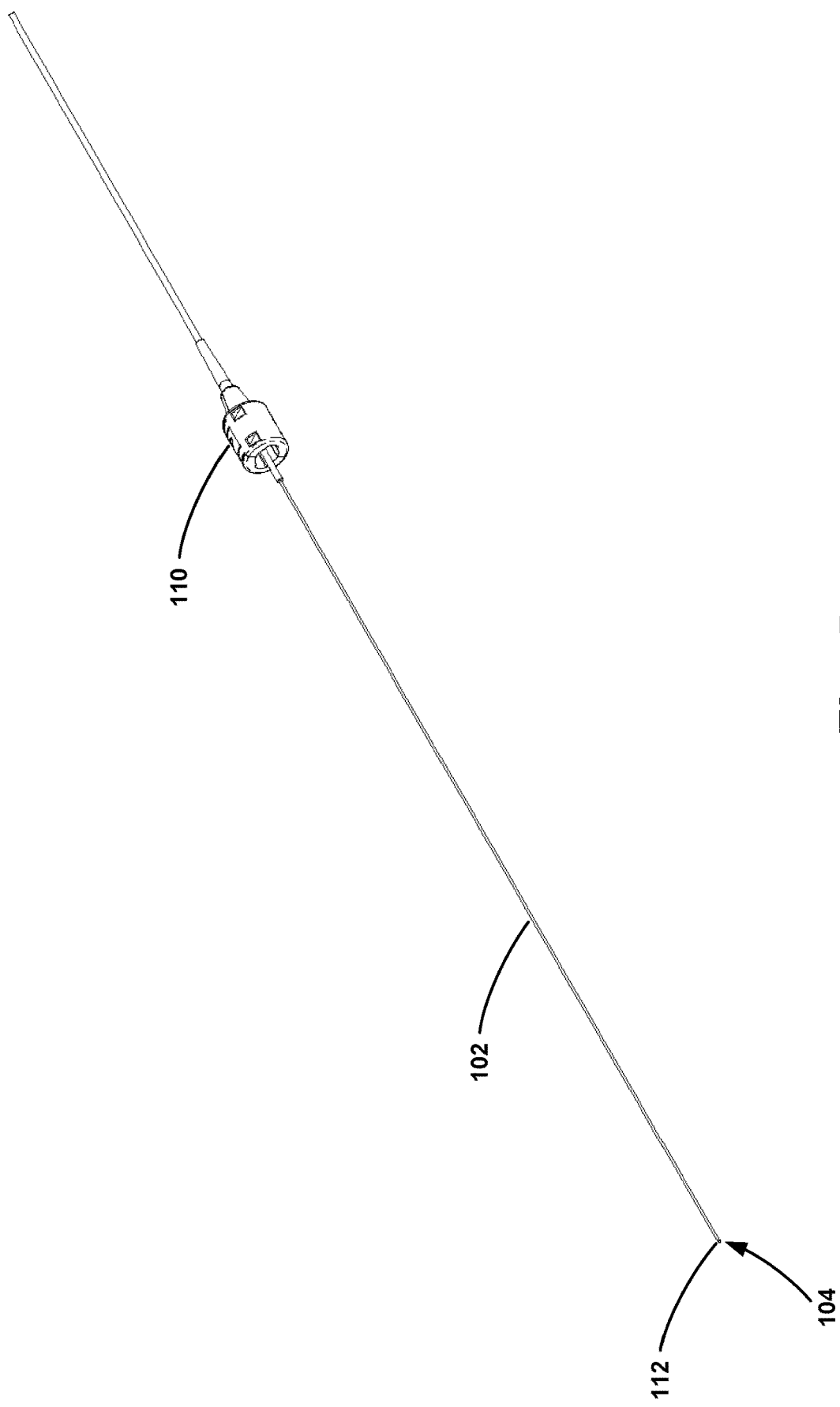
FIG. 5 is a perspective view of a distal portion of the guide wire system of FIG. 4, according to an example.

With reference to the Figures, FIG. 1 is guide wire system 100 according to an example, and FIG. 2 is a cross-sectional view taken along line A-A of the guide wire system of FIG. 1. As shown in FIG. 2, the guide wire system 100 includes a guide wire 102 having a distal end 104 and a proximal end 106. The guide wire system 100 further includes a first connector 108 coupled to the proximal end 106 of the guide wire 102, and a second connector 110 coupled to the guide wire 102 between the distal end 104 and the proximal end 106. An electromagnetic sensor 112 is coupled to the distal end 104 of the guide wire 102. The guide wire system 100 further includes a polymeric tube 114 surrounding at least a portion of the guide wire 102 and at least a portion of the electromagnetic sensor 112. In one example, the guide wire system 100 is discarded after each procedure. In another example, the guide wire system 100 can be sanitized and reused after each procedure.

The guide wire 102 comprises a superelastic material. When mechanically loaded, a superelastic material deforms reversibly to high strains (up to 10%) by the creation of a stress-induced phase. When the load is removed, the new phase becomes unstable and the material regains its original shape automatically. As such, the guide wire 102 is configured to (i) transition from a first configuration to a second configuration responsive to a force applied to the guide wire 102, and (ii) return from the second configuration to the first configuration responsive to the force being removed from the guide wire 102. In one particular example, the guide wire 102 has a straight shape in the first configuration and a bent shape in the second configuration. The superelasticity of the guide wire 102 provides kink resistance and tensile strength to the guide wire system 100. In one particular example, the superelastic material comprises a nickel titanium alloy, such as nitinol. Other superelastic materials are possible as well. The guide wire 102 can include a lubricious coating that reduces friction between the guide wire 102 and other components of the guide wire system 100. A diameter of the guide wire 102 ranges from about 0.4 mm to about 1 mm.

In one example, a stiffness of the guide wire 102 is constant along an entire length of the guide wire 102 from the proximal end 106 to the distal end 104. In another example, a stiffness of a distal portion of the guide wire 102 is less than a stiffness of a proximal portion of the guide wire 102. In such an example, a length of the distal portion of the guide wire 102 is less than a length of the proximal portion of the guide wire 102. The reduced stiffness of the distal portion of the guide wire 102 may provide increased flexibility of the distal portion of the guide wire 102, which may be advantageous in certain use cases.

In one example, a diameter of the guide wire 102 is constant along an entire length of the guide wire 102 from the proximal end 106 to the distal end 104. In another example, a diameter of a distal portion of the guide wire 102 is less than a diameter of a proximal portion of the guide wire 102. In such an example, a length of the distal portion of the guide wire 102 is less than a length of the proximal portion of the guide wire 102. The reduced diameter at the distal portion of the guide wire 102 may provide increased flexibility of the distal portion of the guide wire 102, which may be advantageous in certain use cases.

As shown in FIG. 1 and as described above, the guide wire system 100 includes the first connector 108 coupled to the proximal end 106 of the guide wire 102. In one example, the first connector 108 comprises a pin connector, such as a 10-pin connector as a non-limiting example. In another example, the polymeric tube 114 surrounds at least a portion of the first connector 108, and the first connector 108 is secured to the proximal end 106 of the guide wire 102 via a heat bond between the polymeric tube 114 and the guide wire 102. In another example, the guide wire system 100 further includes a second polymeric tube positioned around the guide wire 102 between the first connector 108 and the second connector 110.

The first connector 108 can include a flexible circuit that includes a memory chip configured to transmit an identification of the guide wire system 100 to an image guided surgery system when the first connector 108 is coupled to the image guided surgery system. The flexible circuit comprises an electronic circuit that is assembled by mounting electronic devices on flexible plastic substrates. As examples, the flexible plastic substrate can be formed from at least one material chosen from polyimide, Polyether ether ketone, and transparent conductive polyester film. Such a design enables the circuit board to conform to a desired shape, or to flex during its use.

As shown in FIG. 1 and as described above, the guide wire system 100 includes the second connector 110 coupled to the guide wire 102 between the distal end 104 and the proximal end 106. In one example, the second connector 110 comprises a bayonet connector configured to interact with a complementary bayonet connector of balloon dilation catheter to thereby couple the guide wire system 100 to the balloon dilation catheter. In one particular example, the second connector 110 is coupled to a handpiece of balloon dilation catheter. A geometry of the second connector 110 with respect to the balloon dilation catheter allows a user to set a desired distance between the distal end 104 of the guide wire 102 and a distal end of the balloon dilation catheter. In one example, when the second connector 110 is coupled to the balloon dilation catheter, the distal end 104 of the guide wire 102 is aligned with a distal end of the balloon dilation catheter. In another example, when the second connector 110 is coupled to the balloon dilation catheter, the distal end 104 of the guide wire 102 extends distally from a distal end of the balloon dilation catheter.

Exemplary balloon dilation catheters and methods of use particularly suited for the dilation of anatomic structures associated with the sinuses and use with the guide wire system 100 are disclosed, for example, in U.S. Pat. No. 8,282,667 which is incorporated by reference herein.

As shown in FIG. 1 and as described above, the guide wire system 100 includes an electromagnetic sensor 112 positioned at the distal end 104 of the guide wire 102. When in use, the electromagnetic sensor 112 is configured to interact with an image guided surgery system to transmit data to the image guided surgery system indicating a location of the electromagnetic sensor 112. Since the electromagnetic sensor 112 is positioned at the distal end 104 of the guide wire 102, the transmitted location of the electromagnetic sensor 112 corresponds to a location of the distal end 104 of the guide wire 102. As discussed in additional detail below, this information can be used to ensure a device (such as a balloon dilation catheter) is properly positioned in a desired nasal cavity to thereby treat nasal afflictions such as sinusitis.

In one example, the electromagnetic sensor 112 is potted by an epoxy prior to being coupled to the distal end 104 of the guide wire 102. In another example, the electromagnetic sensor 112 is coupled to the distal end 104 of the guide wire 102 by being potted by an epoxy. Potting the electromagnetic sensor 112 in an epoxy may provide a more robust sensor that is able to better withstand the rigors of multiple nasal cavity procedures. In yet another example, the electromagnetic sensor 112 may be secured to the distal end 104 of the guide wire 102 via a radio frequency (RF) tipping die. Utilizing an RF tipping die provides a benefit of joining the electromagnetic sensor 112 to the distal end 104 of the guide wire 102 without the use of adhesive. Further, the RF tipping die prevents movement of the electromagnetic sensor 112 as the RF tipping die joins the electromagnetic sensor 112 to the polymeric tube 114.

In one example, the guide wire system 100 further includes a camera positioned at the distal end 104 of the guide wire 102. In such an example, the electromagnetic sensor 112 may work in combination with the camera to provide a medical professional with the location of the distal end 104 of the wide wire 102.

In another example, a method of manufacturing the guide wire system 100 of any of the examples described above is provided. The method may include (a) positioning a first connector 108 at a proximal end 106 of a guide wire 102, wherein the guide wire 102 comprises a superelastic material that is configured to (i) transition from a first configuration to a second configuration responsive to a force applied to the guide wire 102 and (ii) return from the second configuration to the first configuration responsive to the force being removed from the guide wire 102, (b) positioning a second connector 110 on the guide wire 102 between a distal end 104 of the guide wire 102 and the proximal end 106 of the guide wire 102, (c) positioning an electromagnetic sensor 112 at the distal end 104 of the guide wire 102, (d) positioning a polymeric tube 114 around at least a portion of the guide wire 102 and at least a portion of the electromagnetic sensor 112, and (e) applying a heat source to at least a portion of the polymeric tube 114.

In one example of the method described above, applying the heat source to at least a portion of the polymeric tube 114 comprises applying the heat source adjacent the proximal end 106 of the guide wire 102 to secure the first connector 108 to the proximal end 106 of the guide wire 102. In another example of the method, applying the heat source to at least a portion of the polymeric tube 114 comprises applying the heat source adjacent the distal end 104 of the guide wire 102 to secure the electromagnetic sensor 112 to the distal end 104 of the guide wire 102.

As described above, the electromagnetic sensor 112 is potted in epoxy prior to being coupled to the distal end 104 of the guide wire 102. In another example, the electromagnetic sensor 112 is coupled to the distal end 104 of the guide wire 102 by being potted in epoxy. In yet another example, the electromagnetic sensor 112 is secured to the distal end 104 of the guide wire 102 via a radio frequency tipping die.

In one example, a method of treating a sinus cavity of a subject is disclosed. The method includes (a) inserting a distal portion of a guide wire system into a lumen of a balloon dilation catheter, the guide wire system including: (i) a guide wire having a distal end and a proximal end, wherein the guide wire comprises a superelastic material that is configured to (1) transition from a first configuration to a second configuration responsive to a force applied to the guide wire and (2) return from the second configuration to the first configuration responsive to the force being removed from the guide wire, (ii) a first connector coupled to the proximal end of the guide wire, (iii) a second connector coupled to the guide wire between the distal end and the proximal end, (iv) an electromagnetic sensor coupled to the distal end of the guide wire, and (v) a polymeric tube surrounding at least a portion of the guide wire and at least a portion of the electromagnetic sensor, and the balloon dilation catheter including: (i) an inner guide member including the lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member, (b) coupling the second connector of the wide wire system to the balloon dilation catheter such the distal end of the guide wire is fixed with respect to a distal end of the balloon dilation catheter, (c) directing the distal end of the guide wire and the distal end of the balloon dilation catheter simultaneously to a drainage pathway of the sinus cavity using data received from the electromagnetic sensor, and (d) inflating the balloon.

In one example, when the second connector 110 is coupled to the balloon dilation catheter, the distal end 104 of the guide wire 102 is aligned with a distal end of the balloon dilation catheter. In another example, when the second connector 110 is coupled to the balloon dilation catheter, the distal end 104 of the guide wire 102 extends distally from a distal end of the balloon dilation catheter. In one example, the method can further include re-positioning the inner guide member based at least in part on a determined location of the distal end 104 of the guide wire 102 with respect to the sinus cavity.

In another example, another method of treating a sinus cavity of a subject is disclosed. The method includes (a) inserting a portion of the guide wire system 100 of any of the examples described above into a nostril of the subject, (b) directing the distal end 104 of the guide wire 102 to a drainage pathway of the sinus cavity using data received from the electromagnetic sensor 112, (c) while the distal end 104 of the guide wire 102 is in the drainage pathway, positioning a balloon dilation catheter over the guide wire 102, the balloon dilation catheter including: (i) an inner guide member including a lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member, (d) directing the inner guide member over the guide wire to the drainage pathway of the sinus cavity, (e) advancing the movable shaft and balloon over the inner guide member to place the balloon in the drainage pathway while keeping the inner guide member static relative to the drainage pathway, and (f) inflating the balloon.

In one example, when the second connector 110 is coupled to the balloon dilation catheter, the distal end 104 of the guide wire 102 is aligned with a distal end of the balloon dilation catheter. In another example, when the second connector 110 is coupled to the balloon dilation catheter, the distal end 104 of the guide wire 102 extends distally from a distal end of the balloon dilation catheter. In one example, the method can further include re-positioning the inner guide member based at least in part on a determined location of the distal end 104 of the guide wire 102 with respect to the sinus cavity.

In yet another example, another method of treating a sinus cavity of a subject is disclosed. The method includes (a) inserting a distal portion of a balloon dilation catheter into a nostril of the subject, the balloon dilation catheter including: (i) an inner guide member including a lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member, (b) directing the inner guide member to a drainage pathway of the sinus cavity, (c) advancing the movable shaft and balloon over the inner guide member to place the balloon in the drainage pathway while keeping the inner guide member static relative to the drainage pathway, (d) while the balloon is in the drainage pathway, inserting the guide wire system 100 of any of the examples described above into the lumen of the inner guide member, (e) advancing the guide wire system through the lumen until the distal end 104 of the guide wire 102 is aligned with a distal end of the inner guide member, and (f) inflating the balloon. In one example, the method can further include re-positioning the inner guide member based at least in part on a determined location of the distal end 104 of the guide wire 102 with respect to the sinus cavity.

Figure 6:
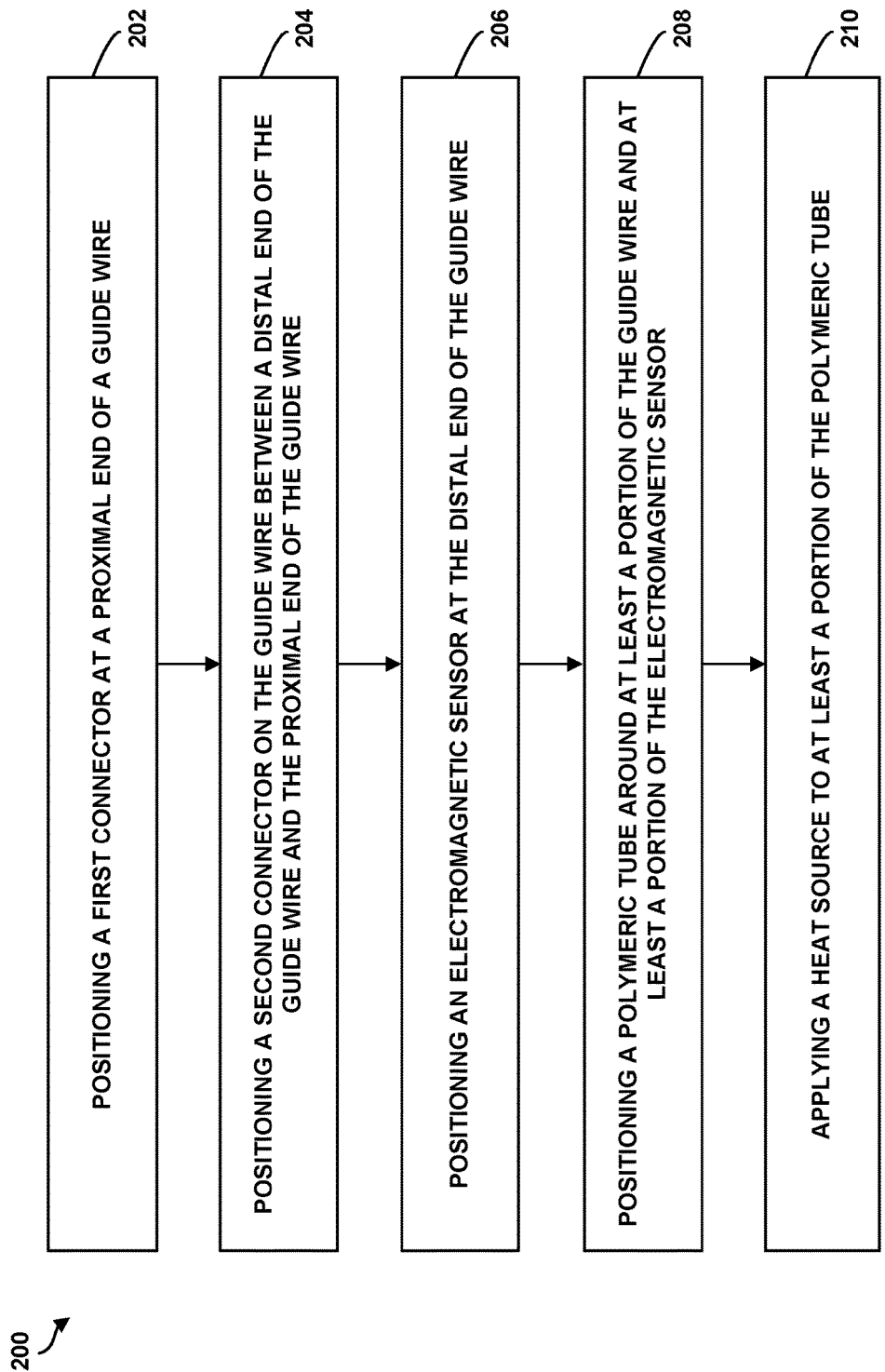
FIG. 6 depicts a flowchart for a method of manufacturing a guide wire system, according to an example.

Referring now to FIG. 6, a flowchart for a method 200 of manufacturing a guide wire system is shown according to an example. The method steps of method 200 may be carried out to manufacture the guide wire system 100 as described above in relation to FIGS. 1-5. Method 200 may include one or more operations, functions, or actions as illustrated by one or more of blocks 202-210. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 6, at block 202, the method 200 includes positioning a first connector 108 at a proximal end 106 of a guide wire 102. As described above in relation to FIGS. 1-5, the guide wire 102 comprises a superelastic material that is configured to (i) transition from a first configuration to a second configuration responsive to a force applied to the guide wire 102 and (ii) return from the second configuration to the first configuration responsive to the force being removed from the guide wire 102. At block 204, the method 200 includes positioning a second connector 110 on the guide wire 102 between a distal end 104 of the guide wire 102 and the proximal end 106 of the guide wire 102. At block 206, the method 200 includes positioning an electromagnetic sensor 112 at the distal end 104 of the guide wire 102. At block 208, the method 200 includes positioning a polymeric tube 114 around at least a portion of the guide wire 102 and at least a portion of the electromagnetic sensor 112. At block 210, the method 200 includes applying a heat source to at least a portion of the polymeric tube 114.

In one example of the method 200 described above, applying the heat source to at least a portion of the polymeric tube 114 comprises applying the heat source adjacent the proximal end 106 of the guide wire 102 to secure the first connector 108 to the proximal end 106 of the guide wire 102. In another example of the method 200, applying the heat source to at least a portion of the polymeric tube 114 comprises applying the heat source adjacent the distal end 104 of the guide wire 102 to secure the electromagnetic sensor 112 to the distal end 104 of the guide wire 102.

As described above, the electromagnetic sensor 112 is potted in epoxy prior to being coupled to the distal end 104 of the guide wire 102. In another example, the electromagnetic sensor 112 is coupled to the distal end 104 of the guide wire 102 by being potted in epoxy. In yet another example, the electromagnetic sensor 112 is secured to the distal end 104 of the guide wire 102 via a radio frequency tipping die.

Figure 7:
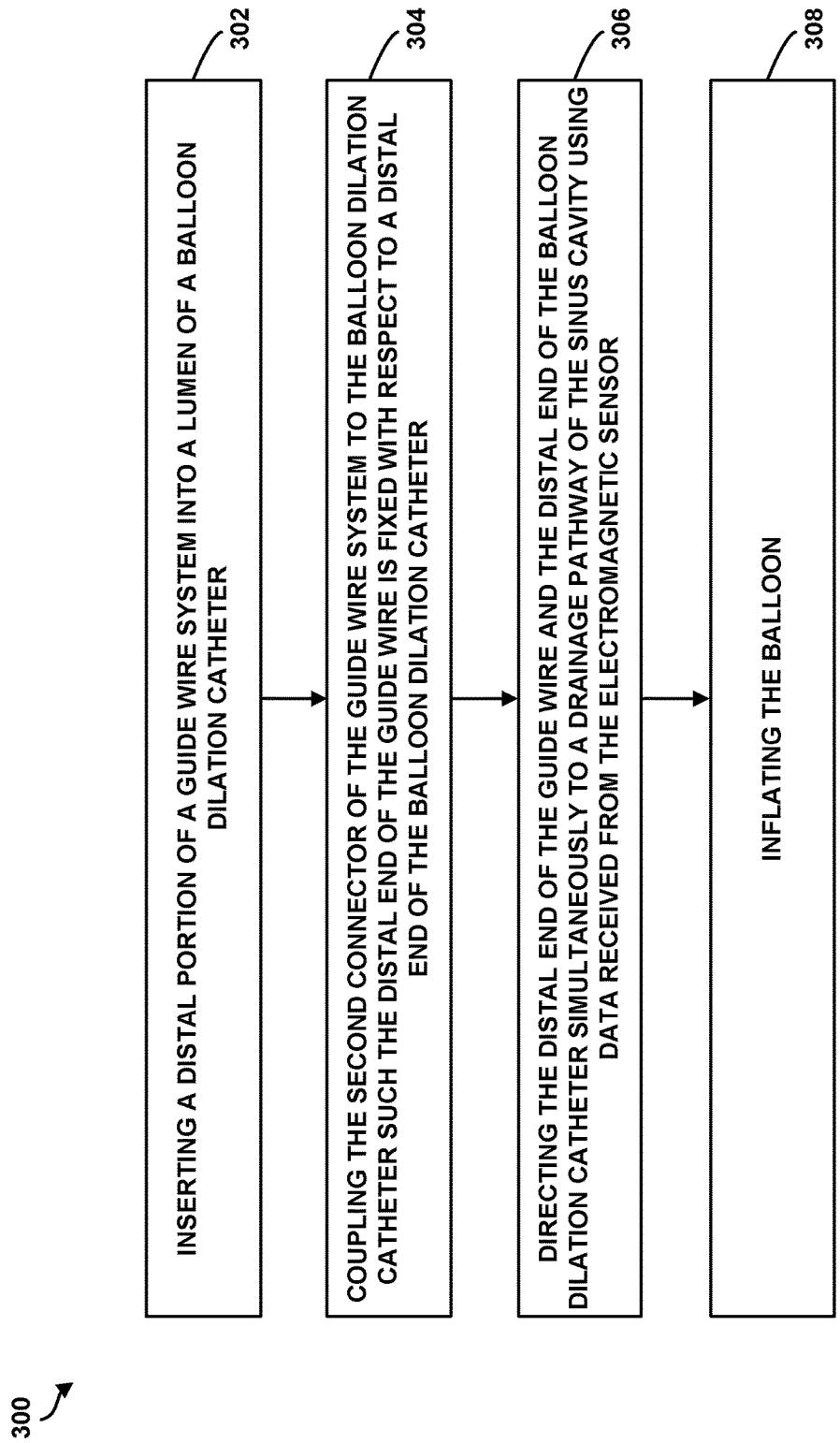
FIG. 7 depicts a flowchart for a method of treating a sinus cavity of a subject, according to an example.

Referring to FIG. 7, a flowchart for a method 300 of treating a sinus cavity of a subject is shown according to an example. The method steps of method 300 may be carried out at least in part by the guide wire system 100 as described above in relation to FIGS. 1-5. Method 300 may include one or more operations, functions, or actions as illustrated by one or more of blocks 302-308. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 7, at block 302 the method 300 includes inserting a distal portion of a guide wire system into a lumen of a balloon dilation catheter. The guide wire system may include any one of the features of the guide wire system 100 described above, including (i) a guide wire having a distal end and a proximal end, wherein the guide wire comprises a superelastic material that is configured to (1) transition from a first configuration to a second configuration responsive to a force applied to the guide wire and (2) return from the second configuration to the first configuration responsive to the force being removed from the guide wire, (ii) a first connector coupled to the proximal end of the guide wire, (iii) a second connector coupled to the guide wire between the distal end and the proximal end, (iv) an electromagnetic sensor coupled to the distal end of the guide wire, and (v) a polymeric tube surrounding at least a portion of the guide wire and at least a portion of the electromagnetic sensor. The balloon dilation catheter includes: (i) an inner guide member including the lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member.

At block 304, the method 300 includes coupling the second connector of the guide wire system to the balloon dilation catheter such the distal end of the guide wire is fixed with respect to a distal end of the balloon dilation catheter. At block 306, the method 300 includes directing the distal end of the guide wire and the distal end of the balloon dilation catheter simultaneously to a drainage pathway of the sinus cavity using data received from the electromagnetic sensor. At block 308, the method includes inflating the balloon.

In one example, when the second connector 110 is coupled to the balloon dilation catheter, the distal end 104 of the guide wire 102 is aligned with a distal end of the balloon dilation catheter. In another example, when the second connector 110 is coupled to the balloon dilation catheter, the distal end 104 of the guide wire 102 extends distally from a distal end of the balloon dilation catheter. In one example, the method 300 can further include re-positioning the inner guide member based at least in part on a determined location of the distal end 104 of the guide wire 102 with respect to the sinus cavity. In another example, the method 300 can further include (i) prior to re-positioning the distal end of the balloon dilation catheter, deflating the balloon, and (ii) re-inflating the balloon once the distal end of the balloon dilation catheter is re-positioned. In one example, the drainage pathway of the sinus comprises the frontal recess of the frontal sinus cavity. Further, in one example the first connector comprises a pin connector, and wherein the second connector comprises a bayonet connector configured to interact with a complementary bayonet connector of the balloon dilation catheter to thereby couple the guide wire system to the balloon dilation catheter.

Figure 8:
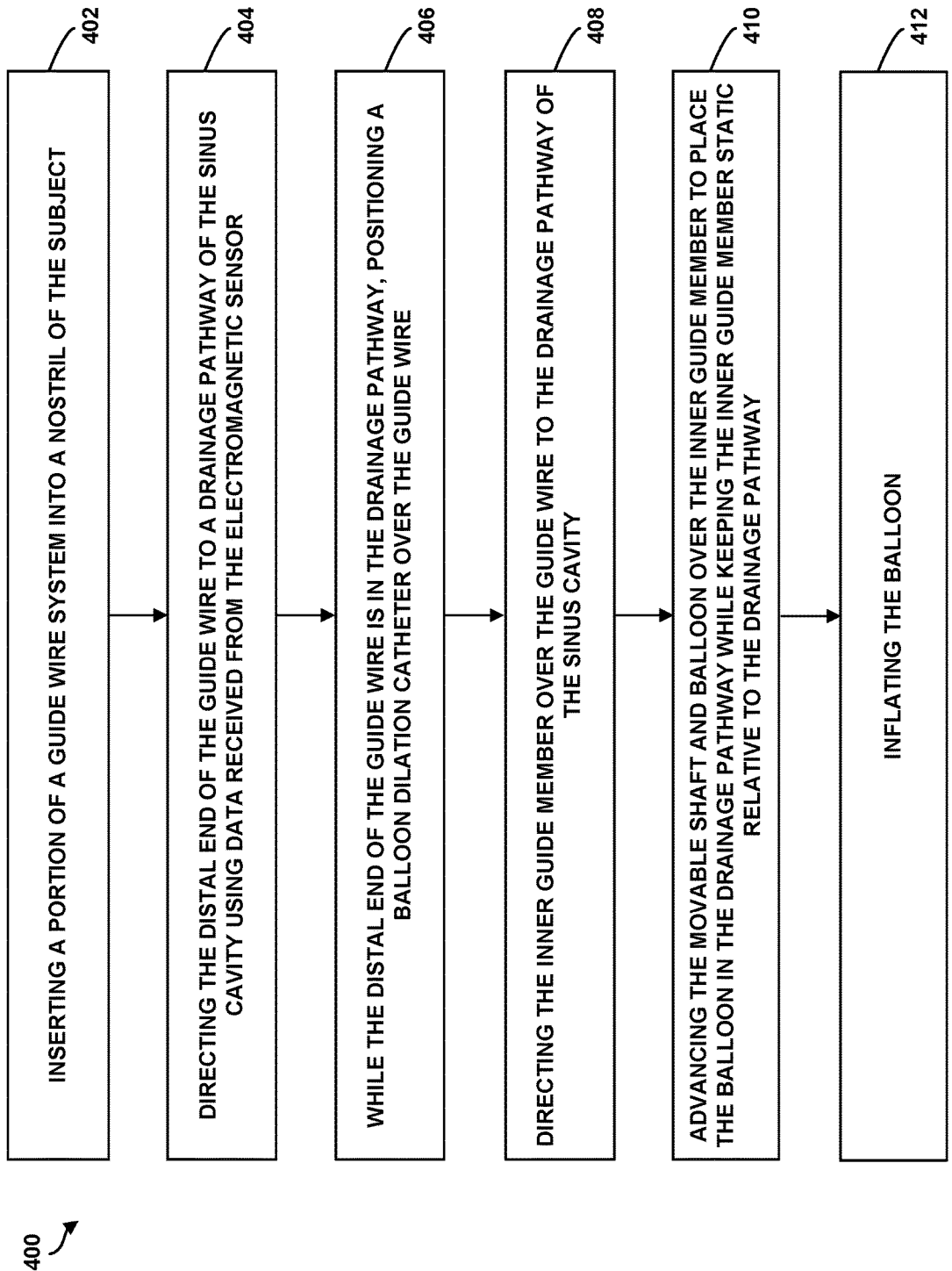
FIG. 8 depicts a flowchart for another method of treating a sinus cavity of a subject, according to an example.

Referring to FIG. 8, a flowchart for another method 400 of treating a sinus cavity of a subject is shown according to an example. The method steps of method 400 may be carried out at least in part by the guide wire system 100 as described above in relation to FIGS. 1-5. Method 400 may include one or more operations, functions, or actions as illustrated by one or more of blocks 402-412. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 8, at block 402 the method 400 includes inserting a portion of the guide wire system 100 of any of the examples described above into a nostril of the subject. At block 404, the method 400 includes directing the distal end 104 of the guide wire 102 to a drainage pathway of the sinus cavity using data received from the electromagnetic sensor 112. At block 406, the method 400 includes, while the distal end 104 of the guide wire 102 is in the drainage pathway, positioning a balloon dilation catheter over the guide wire 102. The balloon dilation catheter includes: (i) an inner guide member including a lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member. At block 408, the method 400 includes directing the inner guide member over the guide wire to the drainage pathway of the sinus cavity. At block 410, the method 400 includes advancing the movable shaft and balloon over the inner guide member to place the balloon in the drainage pathway while keeping the inner guide member static relative to the drainage pathway. At block 412, the method 400 includes inflating the balloon.

In one example, when the second connector 110 is coupled to the balloon dilation catheter, the distal end 104 of the guide wire 102 is aligned with a distal end of the balloon dilation catheter. In another example, when the second connector 110 is coupled to the balloon dilation catheter, the distal end 104 of the guide wire 102 extends distally from a distal end of the balloon dilation catheter. In one example, the method 400 can further include re-positioning the inner guide member based at least in part on a determined location of the distal end 104 of the guide wire 102 with respect to the sinus cavity.

Figure 9:
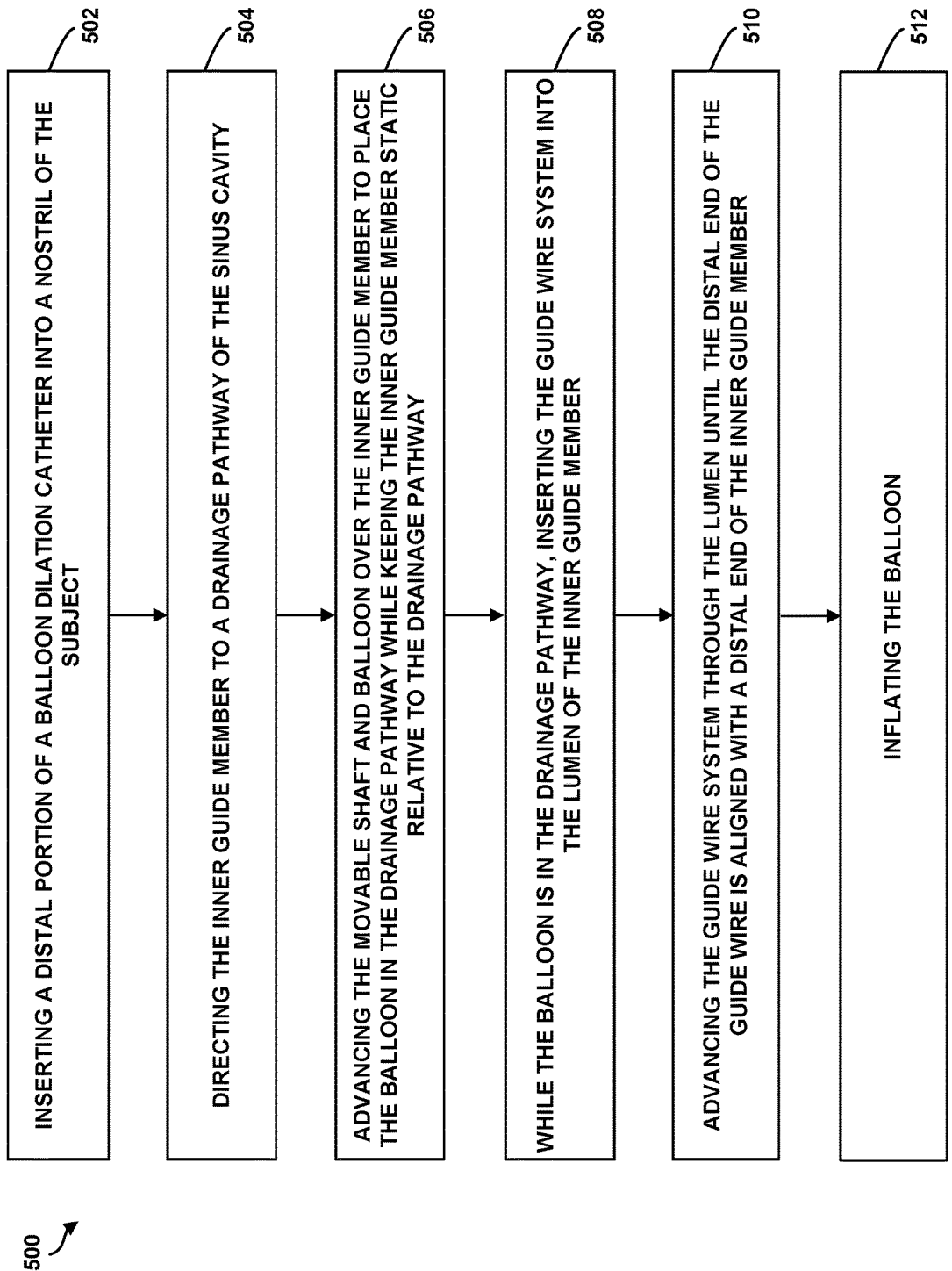
FIG. 9 depicts a flowchart for another method of treating a sinus cavity of a subject, according to an example.

Referring to FIG. 9, a flowchart for another method 500 of treating a sinus cavity of a subject is shown according to an example. The method steps of method 500 may be carried out at least in part by the guide wire system 100 as described above in relation to FIGS. 1-5. Method 500 may include one or more operations, functions, or actions as illustrated by one or more of blocks 502-512. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 9, at block 502 the method 500 includes inserting a distal portion of a balloon dilation catheter into a nostril of the subject. The balloon dilation catheter includes: (i) an inner guide member including a lumen, and (ii) a movable shaft coupled to a balloon and mounted on the inner guide member, wherein the balloon dilation catheter is configured to allow the movable shaft to move along the inner guide member and prevent the movable shaft from rotating around the inner guide member. At block 504, the method 500 includes directing the inner guide member to a drainage pathway of the sinus cavity. At block 506, the method 500 includes advancing the movable shaft and balloon over the inner guide member to place the balloon in the drainage pathway while keeping the inner guide member static relative to the drainage pathway. At block 508, the method 500 includes, while the balloon is in the drainage pathway, inserting the guide wire system 100 of any of the examples described above into the lumen of the inner guide member. At block 510, the method 500 includes advancing the guide wire system through the lumen until the distal end 104 of the guide wire 102 is aligned with a distal end of the inner guide member. At block 512, the method 500 includes inflating the balloon.

In one example, the method 500 can further include re-positioning the inner guide member based at least in part on a determined location of the distal end 104 of the guide wire 102 with respect to the sinus cavity.

The methods described herein can be utilized effectively with any of the examples or variations of the devices and systems described above, as well as with other examples and variations not described explicitly in this document. The features of any of the devices or device components described in any of the examples herein can be used in any other suitable example of a device or device component.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

What is claimed is:

1. A guide wire system comprising:
   a guide wire having a distal end and a proximal end, wherein the guide wire comprises a superelastic material;
   a first connector positioned at and coupled to the proximal end of the guide wire;
   a second connector coupled to the guide wire between the distal end and the proximal end;
   an electromagnetic sensor coupled to the distal end of the guide wire; and
   a polymeric tube surrounding at least a portion of the guide wire and at least a portion of the electromagnetic sensor.

2. The guide wire system of claim 1, wherein the first connector includes a flexible circuit, wherein the flexible circuit includes a memory chip configured to transmit an identification of the guide wire system to an image guided surgery system when the first connector is coupled to the image guided surgery system.

3. The guide wire system of claim 1, wherein the polymeric tube surrounds at least a portion of the first connector, and wherein the first connector is secured to the proximal end of the guide wire via a heat bond between the polymeric tube and the guide wire.

4. The guide wire system of claim 1, wherein the electromagnetic sensor is potted by an epoxy.

5. The guide wire system of claim 1, wherein the electromagnetic sensor is secured to the distal end of the guide wire via a radio frequency tipping die.

6. The guide wire system of claim 1, wherein the second connector is coupled to a handpiece of a balloon dilation catheter, and wherein a geometry of the second connector to the handpiece allows a user to set a desired distance between the distal end of the guide wire and a distal end of the balloon dilation catheter.

7. The guide wire system of claim 1, further comprising a camera positioned at the distal end of the guide wire.

8. The guide wire system of claim 1, wherein the first connector comprises a pin connector.

9. The guide wire system of claim 1, wherein the second connector comprises a bayonet connector configured to interact with a complementary bayonet connector of a balloon dilation catheter to thereby couple the guide wire system to the balloon dilation catheter.

10. The guide wire system of claim 1, wherein the guide wire includes a lubricious coating.

\* \* \* \* \*